United States Patent
Arudra et al.

(10) Patent No.: US 11,439,991 B2
(45) Date of Patent: Sep. 13, 2022

(54) CATALYST COMPOSITIONS FOR AROMATIZING HYDROCARBONS AND PROCESSES FOR PRODUCING AROMATIC COMPOUNDS USING THE CATALYST COMPOSITIONS

(71) Applicants: King Fahd University of Petroleum & Minerals, Dhahran (SA); Saudi Arabian Oil Company, Dhahran (SA)

(72) Inventors: Palani Arudra, Dhahran (SA); Abdullah M. Aitani, Khobar (SA); Yaming Jin, Dhahran (SA); Omer Refa Koseoglu, Dhahran (SA); Muhammad Naseem Akhtar, Dhahran (SA)

(73) Assignees: King Fahd University of Petroleum & Minerals, Dhahran (SA); Saudi Arabian Oil Company, Dhahran (SA)

( * ) Notice: Subject to any disclaimer, the term of this patent is extended or adjusted under 35 U.S.C. 154(b) by 133 days.

(21) Appl. No.: 16/720,338

(22) Filed: Dec. 19, 2019

(65) Prior Publication Data

US 2021/0187487 A1    Jun. 24, 2021

(51) Int. Cl.
*C07C 2/76* (2006.01)
*B01J 23/08* (2006.01)
(Continued)

(52) U.S. Cl.
CPC .............. *B01J 29/405* (2013.01); *B01J 23/08* (2013.01); *B01J 35/1019* (2013.01);
(Continued)

(58) Field of Classification Search
CPC ........ B01J 29/405; B01J 23/08; B01J 35/002; B01J 35/1019; B01J 35/1038;
(Continued)

(56) References Cited

U.S. PATENT DOCUMENTS 3,756,942 A * 9/1973 Cattanach ................ B01J 29/40
                                                    208/137
3,789,025 A * 1/1974 Tauster ................ B01J 37/0207
                                                    502/355
(Continued)

FOREIGN PATENT DOCUMENTS

WO    2011131647 A1    10/2011
WO    2017121792 A1    7/2017

OTHER PUBLICATIONS

Munnik et al., "Recent Developments in the Synthesis of Supported Catalysts", American Chemical Society, Chemical Review, vol. 115, pp. 6687-6718, Jun. 19, 2015.
(Continued)

*Primary Examiner* — In Suk C Bullock
*Assistant Examiner* — Jason Y Chong
(74) *Attorney, Agent, or Firm* — Dinsmore & Shohl LLP

(57) ABSTRACT

Processes for aromatizing hydrocarbons include contacting the hydrocarbons with a catalyst composition comprising a metal oxide dispersed on a surface of a zeolite support, where contacting the hydrocarbons with the catalyst composition causes at least a portion of the hydrocarbons to undergo a chemical reaction to form aromatic hydrocarbons. The catalyst composition is prepared by a synthesis process that includes combining the zeolite support with a hydrocarbon solvent to form a zeolite mixture, where the hydrocarbon solvent pre-wets the pores of the zeolite support. The synthesis process further includes combining a polar solvent comprising a metal salt with the zeolite mixture to form an impregnated zeolite support. The synthesis process also
(Continued)

includes drying the impregnated zeolite support and calcining the impregnated zeolite support to convert the metal salt to the metal oxide, thereby forming the catalyst composition.

15 Claims, 3 Drawing Sheets

(51) Int. Cl.
*B01J 37/02* (2006.01)
*B01J 29/40* (2006.01)
*B01J 35/10* (2006.01)
*B01J 37/08* (2006.01)

(52) U.S. Cl.
CPC ....... *B01J 35/1038* (2013.01); *B01J 35/1061* (2013.01); *B01J 37/0207* (2013.01); *B01J 37/0236* (2013.01); *B01J 37/088* (2013.01); *C07C 2/76* (2013.01); *B01J 2229/186* (2013.01); *C07C 2523/08* (2013.01); *C07C 2529/40* (2013.01)

(58) Field of Classification Search
CPC ................ B01J 35/1061; B01J 37/0203; B01J 37/0207; B01J 37/0236; B01J 37/088; B01J 2229/186; C07C 2/76; C07C 2523/08; C07C 2529/40; C07C 5/412
See application file for complete search history.

(56) References Cited

U.S. PATENT DOCUMENTS

| | | | |
|---|---|---|---|
| 4,861,933 A * | 8/1989 | Nemet-Mavrodin | ........................ B01J 29/405 585/419 |
| 5,650,371 A * | 7/1997 | Culross | ................ B01J 37/0201 502/305 |
| 9,242,233 B2 | 1/2016 | Ghosh et al. | |
| 2008/0255398 A1 | 10/2008 | Stevenson et al. | |
| 2017/0087540 A1* | 3/2017 | Ilias | ........................ C07C 5/415 |
| 2017/0114288 A1 | 4/2017 | Ravishankar et al. | |
| 2017/0144138 A1 | 5/2017 | Arvind et al. | |

OTHER PUBLICATIONS

Van der Meer et al., "Dispersion of Co3O4 nanoparticles within SBA-15 using alkane solvents", Microporous and Mesoporous Materials vol. 118 183-188, 2009.
International Search Report and Written Opinion dated Apr. 7, 2021 pertaining to International application No. PCT/US2020/059108 filed Nov. 5, 2020, 15 pgs.
Hambali, H. U. et al. "Enhanced dry reforming of methane over mesostructured fibrous Ni/MFI zeolite: Influence of preparation methods" Journal of the Energy Institute, vol. 93, No. 4, Aug. 1, 2020, pp. 1535-1543.

* cited by examiner

CATALYST COMPOSITIONS FOR AROMATIZING HYDROCARBONS AND PROCESSES FOR PRODUCING AROMATIC COMPOUNDS USING THE CATALYST COMPOSITIONS

BACKGROUND

Field

The present disclosure generally relates to catalyst compositions and processes for processing hydrocarbons, in particular, catalyst compositions and processes for producing aromatic compounds from hydrocarbons.

Technical Background

Light hydrocarbon feedstocks, such as naphtha, may be converted to greater value chemical products, such as aromatic compounds, through various chemical reactions. Typical hydrocarbon feedstocks contain paraffinic and olefinic hydrocarbons that must undergo one or a plurality of chemical conversions before the greater value products are obtained. One such reaction may include aromatization in which non-aromatic hydrocarbons are converted to aromatic hydrocarbons, such as benzene, toluene, ethylbenzene, and xylenes, which may be collectively referred to as "BTEX." These aromatic hydrocarbon compounds may be valuable intermediates for producing plastics, fibers, or other synthetic products.

SUMMARY

Supported catalyst compositions, such as metal oxides supported on zeolite supports, play an integral role in hydrocarbon conversion processes. The performance of supported catalyst compositions incorporated in such processes depend on the methods employed in synthesizing the supported catalyst compositions. Existing supported catalyst compositions can be produced using existing techniques such as thermal spreading, single-solvent impregnation, and wet impregnation. However, these existing techniques for depositing the metal oxide on the catalyst support may result in only a small fraction of the metal oxide infiltrating into the pores of the catalyst support through diffusion, while a greater portion of the metal oxide may deposit on the outer surface of the catalyst support generating large aggregates after drying, calcining or other thermal treatments. Existing methods of producing existing supported catalyst compositions can lead to low dispersion of the metal oxide throughout the catalyst support and the formation of external aggregates, both of which negatively impact the conversion rate of light hydrocarbons to aromatics during a hydrocarbon conversion process. As a result, the quantity of valuable aromatic hydrocarbon compounds produced through the conversion process may be suppressed if such existing catalyst production methods are utilized.

Accordingly, there is an ongoing need for catalyst compositions and processes for aromatizing hydrocarbons with improved catalyst compositions to produce various greater value chemical products, such as aromatic hydrocarbon compounds. The catalyst compositions and processes of the present disclosure may include catalyst compositions prepared by a dual-solvent technique. The catalyst compositions of the present disclosure, for example, may be produced by pre-wetting a zeolite with a hydrocarbon solvent to form a zeolite mixture. The zeolite mixture may be combined with a polar solvent that includes a metal salt to form an impregnated zeolite support. The impregnated zeolite support may be dried and calcined to form a catalyst composition. The catalyst composition may be incorporated into systems and processes for aromatizing hydrocarbons. The catalyst preparation methods of the present disclosure may result in increased amounts of metal oxide dispersed in the catalyst composition compared to existing supported catalyst compositions prepared by existing impregnation techniques. Due to the increased metal oxide dispersion, the catalyst compositions of the present disclosure may provide improved yield of aromatic hydrocarbon compounds from conversion of hydrocarbons through aromatization compared to existing supported catalyst compositions.

According to one or more embodiments of the present disclosure, a process for aromatizing hydrocarbons may include contacting the hydrocarbons with a catalyst composition comprising a metal oxide dispersed on surfaces of a zeolite support. The catalyst composition may be prepared by a synthesis process that may include combining the zeolite support with a hydrocarbon solvent to form a zeolite mixture, where the hydrocarbon solvent pre-wets the pores of the zeolite support. The synthesis process may further include combining a polar solvent comprising a metal salt with the zeolite support to form an impregnated zeolite support, drying the impregnated zeolite support, and calcining the impregnated zeolite support to convert the metal salt to the metal oxide, thereby forming the catalyst composition. Contacting the hydrocarbons with the catalyst composition produced according to such a synthesis process may cause at least a portion of the hydrocarbons to undergo a chemical reaction to form aromatic hydrocarbons According to one or more additional embodiments of the present disclosure, a method of preparing a catalyst composition may include combining a zeolite support with a hydrocarbon solvent to form a zeolite mixture, where the hydrocarbon solvent pre-wets the pores of the zeolite support. The method may further include combining a polar solvent comprising a metal salt with the zeolite mixture to form an impregnated zeolite support. The method may further include drying the impregnated zeolite support. The method may further include calcining the impregnated zeolite support to convert the metal salt to a metal oxide, thereby forming the catalyst composition.

Additional features and advantages of the described embodiments will be set forth in the detailed description that follows, and in part will be readily apparent to those skilled in the art from the description or recognized by practicing the described embodiments, including the detailed description that follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
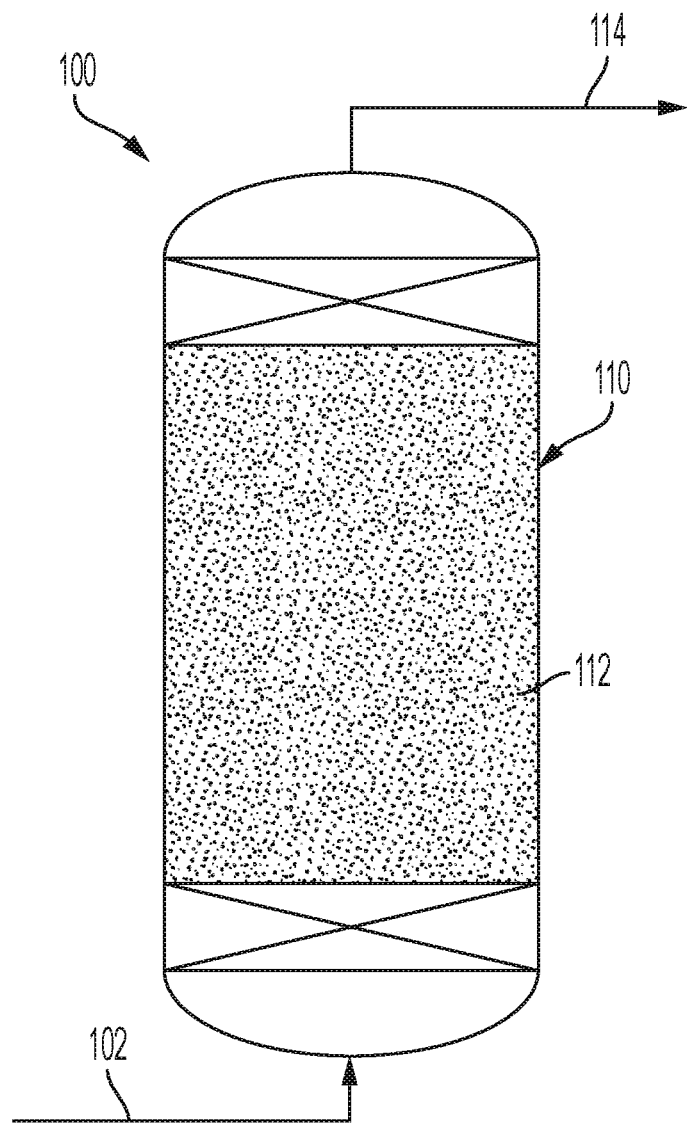
FIG. 1 schematically depicts a fixed bed continuous flow reactor, according to one or more embodiments of the present disclosure.

Reference will now be made in greater detail to various embodiments, some embodiments of which are illustrated in the accompanying drawings.

DETAILED DESCRIPTION

Embodiments of the present disclosure are directed to systems and processes for aromatizing hydrocarbons that include contacting the hydrocarbons with a catalyst composition comprising a metal oxide dispersed on surfaces of a zeolite support, where the catalyst composition is prepared by a two-solvent synthesis process. The two-solvent synthesis process for producing the catalyst composition may include combining the zeolite support with a hydrocarbon solvent to form a zeolite mixture, where the hydrocarbon solvent may pre-wet the pores of the zeolite support. The process may further include combining a polar solvent comprising a metal salt with the zeolite mixture to form an impregnated zeolite support. The process may also include drying the impregnated zeolite support and calcining the impregnated zeolite support to convert the metal salt to the metal oxide, thus forming the catalyst composition. Contacting hydrocarbons with the catalyst compositions prepared by the method of the present disclosure may cause at least a portion of the hydrocarbons to undergo a chemical reaction to form aromatic hydrocarbons. As such, the processes and systems for converting hydrocarbons to aromatic hydrocarbon compounds using the catalyst composition of the present disclosure may produce greater yields of aromatic compounds compared to conversion processes using existing supported catalyst compositions prepared by existing synthesis techniques.

It should be understood that the hydrocarbon feed may be named for its components, and the component for which the feed is named may be the major component of the hydrocarbon feed (such as comprising from 50 weight percent (wt. %), from 70 wt. %, from 90 wt. %, from 95 wt. %, from 99 wt. %, from 99.5 wt. %, or even from 99.9 wt. % of the contents of the hydrocarbon feed to 100 wt. % of the contents of the feed).

As used throughout the present disclosure, the term "catalyst" may refer to any substance that increases the rate of a particular chemical reaction. Catalyst compositions described in the present disclosure may be utilized to promote various reactions, such as the aromatization of non-aromatic hydrocarbons.

As used throughout the present disclosure, the term "hydrocarbon solvent" may refer to any organic liquid solvents that include only hydrogen and carbon atoms. Hydrocarbon solvents described in the present disclosure may be utilized in a dual-solvent technique to pre-wet the pores of a zeolite support. The hydrocarbon solvents described in the present disclosure are immiscible with the polar solvents described in the present disclosure.

Referring now to the process for aromatizing hydrocarbons, the process may include contacting hydrocarbons from a hydrocarbon feed with the catalyst composition of the present disclosure, which includes a metal oxide dispersed on the surfaces of a zeolite support. The hydrocarbon feed may include but is not limited to alkanes, alkenes, alkynes, cycloalkanes, alkadienes, or combinations of these hydrocarbons. The hydrocarbons in the hydrocarbon feed may have from 1 carbon atom to 30 carbon atoms, such as from 1 carbon atom to 20 carbon atoms, from 1 carbon atom to 15 carbon atoms, from 1 carbon atom to 10 carbon atoms, from 2 carbon atoms to 30 carbons atoms, from 2 carbon atoms to 20 carbon atoms, from 2 carbon atoms to 15 carbon atoms, from 1 carbon atom to 10 carbon atoms, from 4 carbon atoms to 20 carbon atoms, or from 4 carbon atoms to 10 carbon atoms. For example, and not by way of limitation, the hydrocarbon feed to be contacted with the catalyst composition may include one or more of methane, ethane, ethene, ethyne, propane, propene, propyne, butane, butene, butyne, pentane, pentene, pentyne, hexane, hexene, hexyne, cyclohexane, cyclohexene, heptane, heptene, heptyne, octane, octene, octyne, nonane, nonene, nonyne, and combinations of these hydrocarbons.

The hydrocarbon feed may include one or more intermediate streams from a hydrocarbon processing facility, such as but not limited to light naphtha, heavy naphtha, or combinations of these. In one or more embodiments, the hydrocarbon feed may include light naphtha comprising at least 50 wt. % alkanes and having a boiling point temperature of from 30 degrees Celsius (° C.) to 90° C., based on the total weight of the hydrocarbon feed. In one or more embodiments, the hydrocarbon feed may include from 50 wt. % to 99.9 wt. % alkanes, from 55 wt. % to 99.9 wt. % alkanes, from 60 wt. % to 99.9 wt. % alkanes, from 65 wt. % to 99.9 wt. % alkanes, from 70 wt. % to 99.9 wt. % alkanes, or from 75 wt. % to 99.9 wt. % alkanes, based on the total weight of the hydrocarbon feed. In one or more embodiments, the hydrocarbon feed may include from 50 wt. % to 99.9 wt. % $C_5$ and $C_6$ hydrocarbons, such as from 55 wt. % to 99.9 wt. % $C_5$ and $C_6$ hydrocarbons, from 60 wt. % to 99.9 wt. % $C_5$ and $C_6$ hydrocarbons, from 65 wt. % to 99.9 wt. % $C_5$ and $C_6$ hydrocarbons, from 70 wt. % to 99.9 wt. % $C_5$ and $C_6$ hydrocarbons, or from 75 wt. % to 99.9 wt. % $C_5$ and $C_6$ hydrocarbons, based on the total weight of the hydrocarbon feed.

The catalyst composition may include a metal oxide dispersed on the surfaces of the zeolite support. The catalyst composition may include one or more oxides of a metal selected from groups 4 to 13 of the International Union of Pure and Applied Chemistry (IUPAC) periodic table, such as groups 8 to 13 of the IUPAC periodic table. In one or more embodiments, the metal of the one or more metal oxides may be a metal selected from groups 4 to 13 and periods 4 to 6 of the IUPAC periodic table, such as period 4 of the periodic table. The metal of the metal oxide may include, but is not limited to, titanium, vanadium, chromium, manganese, iron, cobalt, nickel, copper, zinc, gallium, molybdenum, palladium, silver, hafnium, tungsten, platinum, gold, or combinations of these metals. In one or more embodiments, the metal of the one or more metal oxides may include gallium, zinc, iron, hafnium, or combinations of these metals. In one or more embodiments, the metal oxide may be gallium.

The metal oxide may be dispersed on the surfaces of the zeolite support. The surfaces of the zeolite support may include the outer surfaces of the zeolite support as well as the surfaces of the pores extending into the zeolite support. The catalyst composition may include an amount of the metal oxide dispersed on the on the surfaces of the zeolite support that is sufficient to cause at least a portion of the hydrocarbons to undergo a chemical reaction to form aromatic hydrocarbons. The catalyst composition may include from 1 wt. % to 50 wt. % metal oxide, based on the total weight of the catalyst composition. For example, the catalyst composition may include from 1 wt. % to 45 wt. %, from 1 wt. % to 40 wt. %, from 1 wt. % to 35 wt. %, from 1 wt. % to 30 wt. %, from 1 wt. % to 25 wt. %, from 5 wt. % to 50 wt. %, from 10 wt. % to 50 wt. %, from 15 wt. % to 50 wt. %, from 20 wt. % to 50 wt. %, from 25 wt. % to 50 wt. %, from 5 wt. % to 25 wt. %, from 10 wt. % to 20 wt. % metal oxide, based on the total weight of the catalyst composition.

The zeolite support may include faujasite (FAU) zeolites, mordenite framework inverted (MFI) zeolites, Beta (*BEA) zeolites, or combinations of these zeolite types. In one or more embodiments, the zeolite support includes an MFI type zeolite selected from ZSM-5, ZSM-11, ZSM-12, ZSM-22, ZSM-23, ZSM-35, ZSM-48, ZSM-50, or combinations of these MFI-type zeolites. In one or more embodiments, the zeolite support may be a ZSM-5 zeolite. The zeolite support may include any zeolitic material having an average pore size of less than 2.0 nanometers (nm), such as from 0.30 nm to 2.0 nm, from 0.35 nm to 2.0 nm, from 0.40 nm to 2.0 nm, from 0.45 nm to 2.0 nm, from 0.5 nm to 2.0 nm, from 0.30 nm to 1.90 nm, from 0.30 nm to 1.80 nm, from 0.30 nm to 1.70 nm, from 0.30 nm to 1.60 nm, from 0.30 nm to 1.50 nm, from 0.30 nm to 1.40 nm, from 0.30 nm to 1.30 nm, from 0.30 nm to 1.20 nm, from 0.30 nm to 1.10 nm, from 0.30 nm to 1.0 nm, from 0.30 nm to 0.90 nm, from 0.30 nm to 0.80 nm, from 0.30 nm to 0.70 nm, from 0.35 nm to 0.70 nm, from 0.40 nm to 0.70 nm, from 0.45 nm to 0.65 nm, or from 0.50 nm to 0.60 nm.

The zeolite support may include a molar ratio of silica to alumina of from 5:1 to 50:1, or any ratio between 5:1 and 50:1. In one or more embodiments, the molar ratio of silica to alumina of the zeolite support may range from 10:1 to 50:1, from 15:1 to 50:1, from 20:1 to 50:1, from 25:1 to 50:1, from 5:1 to 45:1, from 5:1 to 40:1, from 5:1 to 35:1, from 10:1 to 45:1, from 15:1 to 40:1, from 20:1 to 35:1, from 25:1 to 35:1, from 26:1 to 34:1, from 27:1 to 33:1, from 28:1 to 32:1, or from 29:1 to 31:1. In one or more embodiments, the molar ratio of silica to alumina of the zeolite support may be 30:1.

Referring now to the synthesis process for preparing the catalyst composition, the catalyst composition may be prepared according to the synthesis process that includes combining the zeolite support with a hydrocarbon solvent to form a zeolite mixture. In the zeolite mixture, the hydrocarbon solvent may pre-wet the pores of the zeolite support. The synthesis process may further include forming a metal salt mixture comprising the metal salt and the polar solvent. The synthesis process may further include combining the metal salt mixture having the polar solvent and the metal salt with the zeolite mixture to form an impregnated zeolite support mixture. The impregnated zeolite support mixture may include the impregnated zeolite support, which may include the metal salt deposited onto the surfaces of the zeolite support, such as the outer surface and pore surfaces of the zeolite support. The synthesis method may further include drying the impregnated zeolite support and calcining the impregnated zeolite support to convert the metal salt to the metal oxide, thereby forming the catalyst composition. The synthesis process of preparing the catalyst composition may result in greater dispersion of the metal oxide across the surfaces of zeolite support, which, in turn, may increase the yield of aromatic hydrocarbons.

The hydrocarbon solvent may include any aliphatic hydrocarbons, cyclic hydrocarbons, or aromatic hydrocarbons capable of forming a mixture and pre-wetting the pores of the zeolite support once the zeolite support is introduced to the hydrocarbon solvent. The hydrocarbon solvent may be selected based on the Hildebrand solubility parameters of the hydrocarbon solvent. The Hildebrand solubility parameter provides an indication of the polarity of a solvent. In embodiments, the hydrocarbon solvent may have a Hildebrand solubility parameter from 14.0 megapascals$^{1/2}$ (MPa$^{1/2}$) to 19.0 MPa$^{1/2}$, such as from 14.0 MPa$^{1/2}$ to 18.5 MPa$^{1/2}$, from 14.0 MPa$^{1/2}$ to 18.0 MPa$^{1/2}$, from 14.0 MPa$^{1/2}$ to 17.5 MPa$^{1/2}$, from 14.0 MPa$^{1/2}$ to 17.0 MPa$^{1/2}$, from 14.0 MPa$^{1/2}$ to 16.5 MPa$^{1/2}$, from 14.0 MPa$^{1/2}$ to 17.0 MPa$^{1/2}$, from 14.0 MPa$^{1/2}$ to 16.5 MPa$^{1/2}$, from 14.0 MPa$^{1/2}$ to 16.0 MPa$^{1/2}$, from 14.0 MPa$^{1/2}$ to 15.5 MPa$^{1/2}$, from 14.0 MPa$^{1/2}$ to 15.0 MPa$^{1/2}$, or from 14.5 MPa$^{1/2}$ to 15.0 MPa$^{1/2}$.

The hydrocarbon solvent may include an alkane having the chemical formula $C_nH_{2n+2}$, where n is from 3 to 12, such as from 4 to 12, from 5 to 12, from 6 to 12, from 3 to 11, from 3 to 10, from 3 to 9, from 3 to 8, from 3 to 7, from 3 to 6, from 4 to 8, or from 5 to 7. In one or more embodiments, the hydrocarbon solvent may include, but is not limited to, n-hexane, n-pentane, n-heptane, cyclohexane, n-octane, iso-octane, benzene, toluene, xylene, or combinations of these hydrocarbon solvents. In one or more embodiments, the hydrocarbon solvent may be n-hexane.

The zeolite mixture may be formed by combining the zeolite support and the hydrocarbon solvent. In one or more embodiments, the zeolite mixture may be mixed while combining the zeolite support with the hydrocarbon solvent. The mixing time of the zeolite mixture may be sufficient to distribute the zeolite support throughout the hydrocarbon solvent and to enable the hydrocarbon solvent to fully pre-wet the pores of the zeolite support. In embodiments, the mixing time may be from 1 minute to 30 minutes, such as from 5 minutes to 30 minutes, from 10 minutes to 30 minutes, from 15 minutes to 30 minutes, from 20 minutes to 30 minutes, from 1 minute to 25 minutes, from 1 minute to 20 minutes, from 1 minute to 15 minutes, from 5 minutes to 25 minutes, from 10 minutes to 20 minutes, or 15 minutes. In one or more embodiments, the zeolite mixture may consist of or consist essentially of the zeolite support and a hydrocarbon solvent selected from the group consisting of n-hexane, n-pentane, n-heptane, cyclohexane, n-octane, iso-octane, benzene, toluene, and xylene.

The metal salt mixture may be prepared and may include the polar solvent and the metal salt, which may be a precursor to the metal oxide of the catalyst composition. The polar solvent may include any solvent that is immiscible with the hydrocarbon solvent. For example, the polar solvent may have a dielectric constant greater than 10, such as greater than 12.5, greater than 15, greater than 17.5, or greater than 20. In embodiments, the polar solvent may have a Hildebrand solubility parameter from 15.0 MPa$^{1/2}$ to 50.0 MPa$^{1/2}$, such as from 17.5 MPa$^{1/2}$ to 50.0 MPa$^{1/2}$, from 20.0 MPa$^{1/2}$ to 50.0 MPa$^{1/2}$, from 22.5 MPa$^{1/2}$ to 50.0 MPa$^{1/2}$, from 25.0 MPa$^{1/2}$ to 50.0 MPa$^{1/2}$, from 27.5 MPa$^{1/2}$ to 50.0 MPa$^{1/2}$, from 30.0 MPa$^{1/2}$ to 50.0 MPa$^{1/2}$, from 32.5 MPa$^{1/2}$ to 50.0 MPa$^{1/2}$, from 35.0 MPa$^{1/2}$ to 50.0 MPa$^{1/2}$, from 37.5 MPa$^{1/2}$ to 50.0 MPa$^{1/2}$, from 40.0 MPa$^{1/2}$ to 50.0 MPa$^{1/2}$, from 42.5 MPa$^{1/2}$ to 50.0 MPa$^{1/2}$, from 45.0 MPa$^{1/2}$ to 50.0 MPa$^{1/2}$, or from 47.5 MPa$^{1/2}$ to 50.0 MPa$^{1/2}$.

The polar solvent may include a halogenated hydrocarbon, water, or combinations of such polar solvents. The halogenated hydrocarbons may include, but are not limited to chloromethane, dichloromethane, 1,1-dichloroethylene, ethylene dichloride, chloroform, 1,1-dichloroethane, trichloroethane, carbon tetrachloride, chlorobenzene, o-dichlorobenzene, 1,1,2-trichlorotrifluoroethane, or combinations of such halogenated hydrocarbons. In one or more embodiments, the polar solvent may be water.

The metal salt present in the metal salt mixture may include any of the previously described metals, which can result in the formation of the metal oxide of the impregnated zeolite support. The metal salts may include nitrates, chlorides, or sulfates of metals selected from groups 4 to 13 of the IUPAC periodic table, such as groups 8 to 13 of the IUPAC periodic table. In one or more embodiments, the metal of the metal salt may be selected from groups 4 to 13 and periods 4 to 6 of the IUPAC periodic table, such as period 4 of the IUPAC periodic table. For example, the metal of the metal salt may include nitrates, chlorides, or sulfates of metals selected from titanium, vanadium, chromium, manganese, iron, cobalt, nickel, copper, zinc, gallium, molybdenum, palladium, silver, hafnium, tungsten, platinum, gold, or combinations of these metals. In one or more embodiments, the metal salts include gallium, zinc, iron, hafnium, or combinations of these metals. In one or more embodiments, the metal salt may be gallium nitrate.

The metal salt mixture, which may include the polar solvent and the metal salt, may then be combined with the previously described zeolite mixture to form the impregnated zeolite support mixture. Combining the metal salt mixture with the zeolite mixture may cause the metal salt to deposit on the surfaces of the zeolite support, with at least a portion of the metal salt diffusing into the pores of the zeolite support to deposit on the pore surfaces. The impregnated zeolite support mixture may include the hydrocarbon solvent, the polar solvent, and the zeolite support having the metal salt deposited on surfaces of the zeolite support. In one or more embodiments, the impregnated zeolite support mixture may consist of or consist essentially of the hydrocarbon solvent, the polar solvent, and the zeolite support having the metal salt deposited on surfaces of the zeolite support.

The impregnated zeolite support may be formed by combining the zeolite mixture and the polar solvent comprising the metal salt. In one or more embodiments, the zeolite mixture may be mixed while combining the metal salt mixture with the zeolite mixture. The impregnated zeolite support mixture may continue to be mixed. The mixing time of the impregnated zeolite support mixture may be sufficient to distribute the zeolite mixture throughout the polar solvent. The mixing time may be from 1 minute to 30 minutes, such as from 5 minutes to 30 minutes, from 10 minutes to 30 minutes, from 15 minutes to 30 minutes, from 20 minutes to 30 minutes, from 1 minute to 25 minutes, from 1 minute to 20 minutes, from 1 minute to 15 minutes, from 5 minutes to 25 minutes, from 10 minutes to 20 minutes, or 15 minutes. The impregnated zeolite support mixture may be heated during mixing to increase the entropy of the impregnated zeolite support mixture, thus decreasing the amount of time needed to form the impregnated zeolite support from the combination of the metal salt mixture and the zeolite mixture. For example, the impregnated zeolite support mixture may be heated to a temperature of from 25° C. to 100° C., such as from 50° C. to 100° C., from 75° C. to 100° C., from 25° C. to 75° C., from 25° C. to 50° C., or from 50° C. to 75° C. during mixing.

Once the impregnated zeolite support is formed according to the above process, the impregnated zeolite support may be dried and calcined to convert the metal salt to the metal oxide, thus forming the catalyst composition having the metal oxide deposited on the outer and pore surfaces of the zeolite support. The drying step in the synthesis process may include drying the impregnated zeolite support at a temperature from 20° C. to 200° C., such as from 50° C. to 150° C., from 75° C. to 125° C., or at 100° C. The drying step may last for a duration from 4 hours to 24 hours, such as from 6 hours to 20 hours, from 8 hours to 16 hours, from 10 hours to 14 hours, or 12 hours.

Upon sufficiently drying the impregnated zeolite support, the impregnated zeolite support may also be calcined, such that the catalyst composition is formed. Calcining the impregnated zeolite support may be conducted at a calcining temperature of from 425° C. to 700° C., from 450° C. to 700° C., from 475° C. to 700° C., from 500° C. to 700° C., from 525° C. to 700° C., from 550° C. to 700° C., from 400° C. to 675° C., from 400° C. to 650° C., from 400° C. to 625° C., from 400° C. to 600° C., from 425° C. to 675° C., from 450° C. to 650° C., from 475° C. to 625° C., from 500° C. to 600° C., or from 525° C. to 575° C. The calcining may last for a duration from 1.0 hour to 12.0 hours, such as from 1.0 hour to 11.0 hours, from 2.0 hours to 10.0 hours, from 3.0 hours to 9.0 hours, from 4.0 hours to 8.0 hours, from 4.5 hours to 7.5 hours, from 5.0 hours to 7.0 hours, from 5.5 hours to 6.5 hours, or 6.0 hours.

The synthesis process described in the present disclosure may produce a catalyst composition with properties suitable for aromatizing hydrocarbons. The catalyst composition may include the metal oxide dispersed across the outer surfaces and pore surfaces of the zeolite support. In one or more embodiments, the catalyst composition may consist of or consist essentially of the metal oxide dispersed onto the outer surfaces and pore surfaces of the zeolite support. The catalyst composition formed by the synthesis method of the present disclosure may have a Brunauer-Emmett-Teller (BET) surface area greater than the BET surface area of existing supported catalyst compositions prepared by wet impregnation or other existing method. The catalyst composition formed by the synthesis method of the present disclosure may have a BET surface area of from 100 square meters per gram ($m^2/g$) to 600 $m^2/g$, such as from 150 $m^2/g$ to 550 $m^2/g$, from 200 $m^2/g$ to 500, from 250 $m^2/g$ to 450 $m^2/g$, from 300 $m^2/g$ to 400 $m^2/g$, from 305 $m^2/g$ to 390 $m^2/g$, from 310 $m^2/g$ to 380 $m^2/g$, from 315 $m^2/g$ to 370 $m^2/g$, from 320 $m^2/g$ to 360 $m^2/g$, from 325 $m^2/g$ to 350 $m^2/g$, from 330 $m^2/g$ to 340 $m^2/g$, or 335 $m^2/g$. The catalyst composition formed by the synthesis method of the present disclosure may have a total pore volume of from 0.10 cubic meters per gram ($cm^3/g$) to 0.50 $cm^3/g$, such as from 0.15 $cm^3/g$ to 0.45 $cm^3/g$, from 0.20 $cm^3/g$ to 0.40 $cm^3/g$, from 0.25 $cm^3/g$ to 0.35 $cm^3/g$, or 0.30 $cm^3/g$. The catalyst composition prepared by the synthesis method of the present disclosure may have an average pore diameter of from 5.0 nanometers (nm) to 50.0 nm, such as from 5.0 nm to 40.0 nm, from 5.0 nm to 30.0 nm, from 5.0 nm to 20.0 nm, from 5.0 nm to 10.0 nm, from 5.0 nm to 9.0 nm, from 5.0 nm to 8.0 nm, from 5.0 nm to 7.5 nm, from 5.0 nm to 7.0 nm, from 5.0 nm to 6.0 nm, from 5.1 nm to 5.9 nm, from 5.2 nm to 5.8 nm, from 5.25 nm to 5.75 nm, from 5.3 nm to 5.6 nm, from 5.35 nm to 5.55 nm, from 5.35 nm to 5.45 nm, or 5.4 nm.

After the catalyst composition has been synthesized according to any of the processes described in the present disclosure, the catalyst composition may be pelletized and sieved, thereby forming a catalyst. In embodiments, additional components, such as a binder or one or more fillers may be added to the catalyst. Binders and fillers may include natural clay, artificial clay, or combinations of natural and artificial clays.

The catalyst may have an average particle size of from 250 μm to 1,250 μm, such as from 275 μm to 1,250 μm, from 300 μm to 1,250 μm, from 325 μm to 1,250 μm, from 350 μm to 1,250 μm, from 375 μm to 1,250 μm, from 400 μm to 1,250 μm, from 425 μm to 1,250 μm, from 450 μm to 1,250 μm, from 475 μm to 1,250 μm, from 500 μm to 1,250 μm, from 250 μm to 1,225 μm, from 250 μm to 1,200 μm, from 250 µm to 1,175 µm, from 250 µm to 1,150 µm, from 250 µm to 1,125 µm, from 250 µm to 1,100 µm, from 250 µm to 1,075 µm, from 250 µm to 1,050 µm, from 250 µm to 1,025 µm, from 250 µm to 1,000 µm, from 275 µm to 1,225 µm, from 300 µm to 1,200 µm, from 325 µm to 1,175 µm, from 350 µm to 1,150 µm, from 375 µm to 1,125 µm, from 400 µm to 1,100 µm, from 425 µm to 1,075 µm, from 450 µm to 1,050 µm, from 475 µm to 1,025 µm, or from 500 µm to 1,000 µm.

The catalyst composition prepared by the synthesis process of the present disclosure may be utilized in a process to convert hydrocarbons to one or more aromatic compounds. The process of the present disclosure for aromatizing hydrocarbons may include contacting hydrocarbons with a catalyst composition comprising a metal oxide dispersed on a surface of a zeolite support within a catalyst system, where contacting the hydrocarbons with the catalyst composition causes at least a portion of the hydrocarbons to undergo a chemical reaction to form aromatic hydrocarbons. The process for converting hydrocarbons to aromatic compounds may further include pretreating the catalyst composition formed according to any of the previously described embodiments. Pretreating the catalyst composition may improve catalyst composition's ability to aromatize hydrocarbons. The catalyst composition may be pretreated under nitrogen or hydrogen flow at a temperature from 400° C. to 700° C. For example, the pretreatment temperature may be from 425° C. to 700° C., from 450° C. to 700° C., from 475° C. to 700° C., from 500° C. to 700° C., from 525° C. to 700° C., from 550° C. to 700° C., from 400° C. to 675° C., from 400° C. to 650° C., from 400° C. to 625° C., from 400° C. to 600° C., from 425° C. to 675° C., from 450° C. to 650° C., from 475° C. to 625° C., from 500° C. to 600° C., or from 525° C. to 575° C. The pretreatment of the catalyst composition may be conducted for a duration from 1.0 hour to 5.0 hours, such as from 1.5 hours to 5.0 hours, from 2.0 hours to 5.0 hours, from 2.5 hours to 5.0 hours, from 1.0 hour to 4.5 hours, from 1.0 hour to 4.0 hours, from 1.0 hour to 3.5 hours, from 1.5 hours to 4.5 hours, from 2.0 hours to 4.0 hours, or from 2.5 hours to 3.5 hours.

Following pretreatment of the catalyst composition, the hydrocarbon feed may be contacted with the catalyst composition under reaction conditions sufficient to cause at least a portion of the hydrocarbons to undergo a chemical reaction to form aromatic hydrocarbons. The contacting may occur within a catalyst system will now be described.

Referring now to FIG. 1, an embodiment of the catalyst system for producing aromatic hydrocarbons from a hydrocarbon feed containing non-aromatic hydrocarbons is illustrated, the catalyst system being designated by reference number 100. The catalyst system 100 may include a reaction zone 110. In one or more embodiments, the reaction zone 110 may be a portion of a reactor that includes the catalyst composition 112 prepared by the synthesis process of the present disclosure. The catalyst system 100 may include one or a plurality of reactors. The reactor or reactors of the catalyst system 100 may include but are not limited to tank or tubular reactors, which may be configured to operate as a batch reactor, a fixed-bed reactor, a continuous stirred-tank reactor (CSTR), or a plug flow reactor. As depicted in FIG. 1, the hydrocarbon feed 102 including one or more non-aromatic hydrocarbons may be introduced to the reaction zone 110, and reactor effluent 114 may be passed out of the reaction zone 110 following contact of the hydrocarbons of the hydrocarbon feed 102 with the catalyst composition 112 in the reaction zone 110. Contacting the hydrocarbons present in the hydrocarbon feed 102 with the catalyst composition 112 in the reaction zone 110 may cause at least a portion of the hydrocarbons from the hydrocarbon feed 102 to undergo a chemical reaction to form aromatic hydrocarbons, which may be present in the reactor effluent 114. The reactor effluent 114 comprising the aromatic hydrocarbons may be passed out of the reaction zone 110.

The hydrocarbon feed 102 may be contacted with the catalyst composition 112 in the reaction zone 110 under reaction conditions sufficient to cause at least a portion of the hydrocarbons to undergo a chemical reaction to form aromatic hydrocarbons. The hydrocarbon feed 102 may be contacted with the catalyst composition 112 in the reaction zone 110 at a reaction temperature from 200° C. to 900° C., such as from 250° C. to 850° C., from 300° C. to 800° C., from 350° C. to 750° C., from 400° C. to 700° C., from 450° C. to 650° C., from 475° C. to 625° C., from 500° C. to 600° C., from 525° C. to 575° C., or at 550° C. The hydrocarbon feed 102 may be contacted with the catalyst composition 112 in the reaction zone 110 at a pressure from 1 bar to 30 bars, such as from 1 bar to 25 bars, from 1 bar to 20 bars, from 1 bar to 15 bars, from 1 bar to 10 bars, or at 5 bars. The hydrocarbon feed 102 may be contacted with the catalyst composition 112 in the reaction zone 110 at a weight hourly space velocity (WHSV) from 0.1 per hour to 20.0 per hour, such as from 0.25 per hour to 15.0 per hour, from 0.5 per hour to 10.0 per hour, from 0.75 per hour to 5.0 per hour, from 0.75 per hour to 2.0 per hour, or from 0.75 per hour to 1.25 per hour.

The reactor effluent 114 may include one or a plurality of aromatic hydrocarbons, such as but not limited to benzene, toluene, ethylbenzene, mixed xylenes (ortho-xylene, meta-xylene, para-xylene, or mixtures of these), and combinations of such hydrocarbons. Benzene, toluene, ethylbenzene, and mixed xylenes may be collectively referred to as "BTEX." In one or more than one embodiment, at least 70% of the hydrocarbons from the hydrocarbon feed undergo a chemical reaction to form aromatic hydrocarbons, such as at least 70.5%, at least 71%, at least 71.5%, at least 72%, at least 72.5%, at least 73%, at least 73.5%, at least 74%, at least 74.5%, or at least 75%. In one or more embodiments, at least 60% of the hydrocarbons undergo a chemical reaction to form BTEX hydrocarbons, such as at least 60.25%, at least 60.5%, at least 60.75%, at least 61%, at least 61.25%, at least 61.5%, at least 61.75%, at least 62%, at least 62.25%, at least 62.5%, at least 62.75%, or at least 63%.

EXAMPLES

The following examples illustrate one or more additional features of the present disclosure described previously. It should be understood that these examples are not intended to limit the scope of the disclosure or the appended claims in any manner.

In the following examples, aromatization catalyst compositions were prepared according to a variety of techniques and characterized for the suitability for aromatizing hydrocarbons.

Example 1—Dual Solvent

A mixture comprising CBV 3024E, a commercially available ZSM-5(30) powder from Zeolyst International (Conshohocken, Pa.) having a silica to alumina ratio of 30:1, was added as the zeolite support to n-hexane to form a suspension. As will be described below, CBV 3024E is denoted with reference number 200 in FIG. 2. The process of adding n-hexane to CBV 3024E pre-wetted the pores of the ZSM- 5(30) powder. Then, a solution comprising gallium nitrate salt dissolved in water was stirred into the suspension to form an impregnated zeolite support. The impregnated zeolite support was stirred for 30 minutes, initially dried at 25° C. for 12 hours, and further dried at 100° C. for an additional 12 hours. The dried impregnated zeolite support was then calcined at 550° C. for six hours to form Example 1, which is denoted with reference number 201 in FIG. 2. The catalyst composition of Example 1 was then pelletized and sieved to catalyst particles having diameters from 500 µm to 1,000 µm and tested in a fixed-bed reactor.

Comparative Example 2—Thermal Spreading

Gallium nitrate was physically mixed with CBV 3024E. The mixture was calcined at 550° C. for six hours to form Comparative Example 2, which is denoted with reference number 202 in FIG. 2. The catalyst of Comparative Example 2 was then pelletized and sieved to particles having diameters from 500 µm to 1,000 µm and tested in a fixed-bed reactor.

Comparative Example 3—Impregnation at 25° C.

Five grams of CBV 3024E was dispersed in 150 milliliters (mL) of water to form a dispersion. A stoichiometric amount of gallium nitrate was added to the dispersion to form a mixture. The mixture was stirred at 25° C. for three hours and subsequently dried at 100° C. for 12 hours. The dried mixture was then calcined at 550° C. for six hours to form Comparative Example 3, which is denoted with reference number 203 in FIG. 2. The catalyst of Comparative Example 3 was then pelletized and sieved to particles having diameters from 500 µm to 1,000 µm and tested in a fixed-bed reactor.

Comparative Example 4—Impregnation at 100° C.

Five grams of CBV 3024E was dispersed in 150 milliliters (mL) of water to form a dispersion. A stoichiometric amount of gallium nitrate was added to the dispersion to form a mixture. The mixture was stirred at 100° C. for three hours and subsequently dried at 100° C. for 12 hours. The dried mixture was then calcined at 550° C. for six hours to form Comparative Example 4, which is denoted with reference number 204 in FIG. 2. The catalyst of Comparative Example 4 was then pelletized and sieved to particles having diameters from 500 µm to 1,000 µm and tested in a fixed-bed reactor.

Comparative Example 5—Wet Impregnation

Five grams of CBV 3024E was mixed with a stoichiometric amount of gallium nitrate in five mL of water. The mixture was dried at 100° C. for 12 hours. The dried mixture was then then calcined at 550° C. for six hours to form Comparative Example 5, which is denoted with reference number 205 in FIG. 2. The catalyst of Comparative Example 5 was then pelletized and sieved to particles having diameters from 500 µm to 1,000 µm and tested in a fixed-bed reactor.

Example 6—Catalyst Characterization

Figure 2:
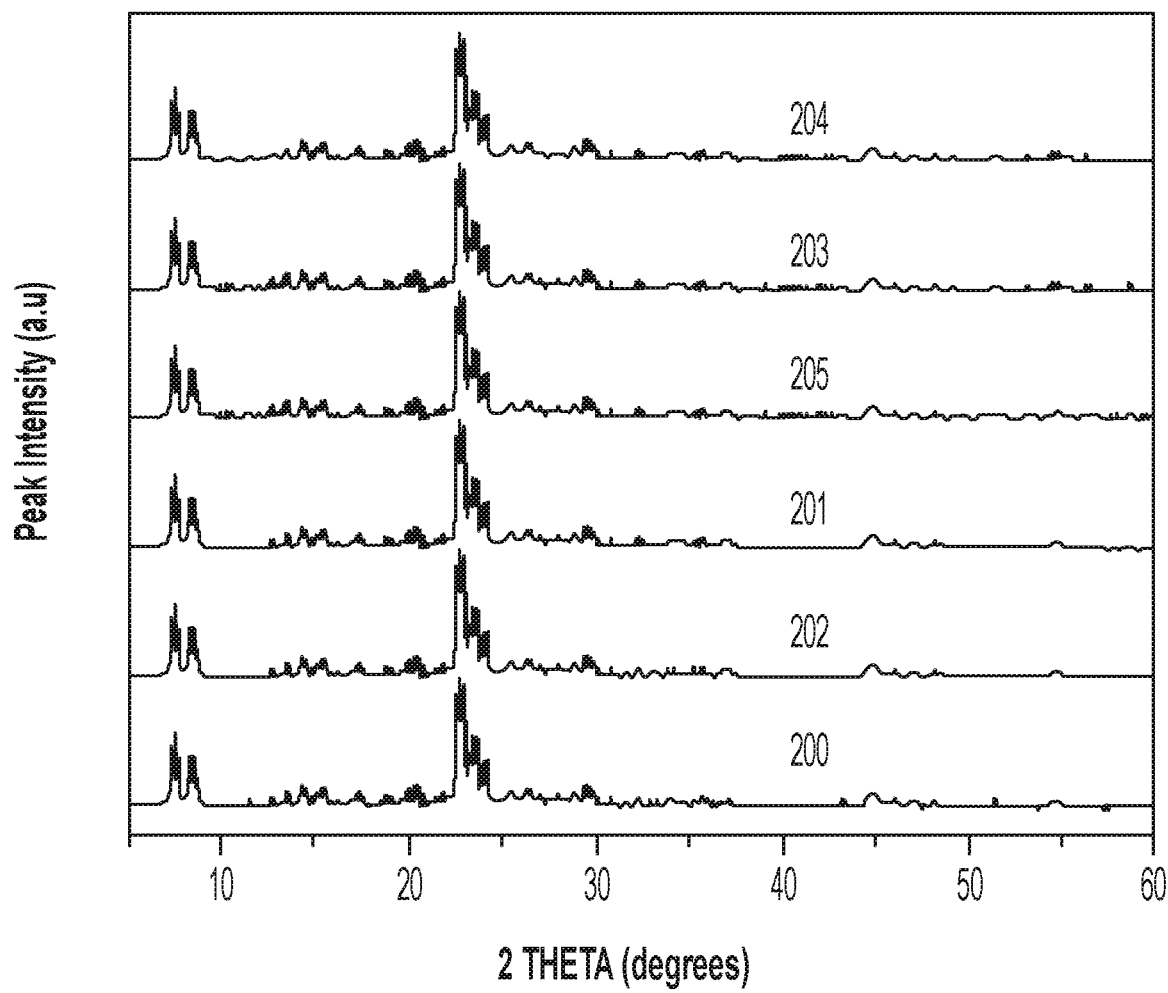
FIG. 2 graphically depicts X-ray diffraction (XRD) patterns of catalyst compositions prepared by existing impregnation techniques and the catalyst composition, according to one or more embodiments described in the present disclosure.

The samples collected from the catalysts of Example 1 and Comparative Examples 2-5 were characterized by powder X-ray diffraction (XRD). The XRD was performed on a Mini-Flex II system, commercially available from Rigaku Corp. (Tokyo, Japan), using nickel filtered CuKα radiation (λ=1.5406 Å) operated in a static scanning mode with a detector angular speed of 2° per minute and a step size of 0.02°. As shown in FIG. 2, the crystallinity of the ZSM-5 remains unchanged for all of the collected samples, both before and after impregnation.

The samples collected from CBV 3024E, Example 1 ("E1"), and Comparative Examples 2-5 ("C. Ex. 2-5") were further characterized according to nitrogen adsorption, which was performed on an Autosorb-1, commercially available from Quantachrome Instruments (Boynton Beach, Fla.). Various physical properties, such as the Brunauer-Emmett-Teller (BET) surface area, the pore volume, and the average pore diameter were determined for each of the samples. The physical properties are described in Table 1, below.

TABLE 1

XRD Patterns of the Parent ZSM-5 sample (CBV 3024E), E1, and C. Ex. 2-5

| Sample | BET Surface Area ($m^2/g$) | Pore Volume ($cm^3/g$) | Average Pore Diameter (nm) |
|---|---|---|---|
| CBV 3024E | 333.1 | 0.27 | 5.33 |
| E1 | 334.5 | 0.29 | 5.40 |
| C. Ex. 2 | 320.1 | 0.27 | 5.50 |
| C. Ex. 3 | 312.1 | 0.27 | 5.22 |
| C. Ex. 4 | 296.5 | 0.25 | 5.17 |
| C. Ex. 5 | 321.3 | 0.30 | 6.03 |

The BET surface area of the catalysts of Comparative Examples 2-5 all decreased compared to the CBV 3024E. However, the catalyst of Example 1 exhibited an increased BET surface area compared to the CBV 3024E. Not intending to be bound by any particular theory, this increased BET surface area of the catalyst of Example 1 prepared according to the methods of the present disclosure may provide a benefit by providing more room to contact hydrocarbons, which may result in a greater conversion rate when compared to similar catalysts having smaller BET surface areas (in other words, the catalysts of Comparative Examples 2-5).

Example 7—Catalyst Reactivity Evaluation

Aromatization of n-hexane utilizing each of CBV 3024E (a zeolite with no gallium oxide), the catalyst of Example 1, and the catalysts of Comparative Examples 2-5 was carried out in a fixed-bed reactor (grade 316 stainless steel with an interior diameter of 0.312 inches, an outer diameter of 0.562 inches, and length of 8 inches). The reactor was separately charged with 0.5 g of the catalyst and activated in a nitrogen flow at a temperature of 550° C. for 1 hour. The n-hexane was introduced to the reactor through a liquid syringe pump to start the reaction, while a constant nitrogen flow of 10 mL per minute was maintained for the duration of the reaction. The conditions of the reactor were 550° C., about 1 bar, and a WHSV of 1 gram per hour for five hours. The quantitative analysis of the reaction products for each of the tested catalysts was performed using a gas chromatogram equipped with two flame ionization detectors.

Complete conversion of n-hexane was observed for all of the tested catalysts after five hours on stream. Table 2, provides the yield for each component of the reactor effluent collected for each of the tested catalysts, which included CBV 3024E, Example 1, and Comparative Examples 2-5.

TABLE 2

Comparison of n-hexane Aromatization for the Prepared Catalyst Samples

| Product Yield | Catalyst | | | | | |
|---|---|---|---|---|---|---|
| | CBV 3024E | E1 | C. Ex. 2 | C. Ex. 3 | C. Ex. 4 | C. Ex. 5 |
| Benzene | 11.5% | 21.2% | 14.6% | 14.4% | 18.2% | 18.7% |
| Toluene | 15.6% | 30.3% | 19.3% | 25.5% | 27.9% | 28.3% |
| Ethylbenzene | 0.5% | 0% | 0.4% | 0% | 0% | 0% |
| m-Xylene | 3.6% | 6.0% | 4.0% | 7.1% | 6.4% | 6.0% |
| p-Xylene | 1.7% | 2.8% | 1.9% | 3.3% | 3.0% | 2.8% |
| o-Xylene | 1.8% | 2.8% | 1.9% | 3.5% | 3.2% | 2.9% |
| BTEX | 34.7% | 63.1% | 42.1% | 53.7% | 58.7% | 58.7% |
| C9+ | 10.2% | 12.0% | 9.9% | 16.4% | 17.0% | 15.1% |
| Methane | 12.0% | 9.9% | 10.4% | 8.0% | 9.9% | 11.2% |
| Ethane | 12.2% | 9.2% | 11.3% | 8.2% | 7.7% | 7.8% |
| Ethylene | 4.2% | 0.9% | 3.7% | 1.2% | 1.1% | 1.1% |
| Propane | 24.0% | 4.1% | 20.5% | 11.2% | 4.9% | 5.3% |
| Propylene | 2.7% | 0.6% | 2.0% | 1.2% | 0.7% | 0.8% |
| Total Paraffins & Olefins | 55.0% | 24.8% | 48.0% | 29.8% | 24.3% | 26.2% |
| Total Aromatics Yield | 45% | 75.2% | 52% | 70.2% | 75.7% | 73.8% |

Notably, Example 1 showed the greatest yields of aromatizing the n-hexane to benzene, toluene, ethylbenzene, and xylene (BTEX) compared to CBV 3024E and Comparative Examples 2-5. BTEX are considered the most valuable aromatic compounds because they increase the research octane number of a gasoline pool while also decreasing the gasoline pool's volatility. Moreover, the total aromatics yield from Example 1 is nearly identical to that of Comparative Example 4. However, Comparative Example 4 results in a C9+ yield that is nearly 42% greater than that produced by Example 1. As is recognized in the art, a C9+ yield is undesirable because C9+ compounds are less valuable as intermediates in downstream processes. As a result, Example 1 may be a more valuable catalyst for aromatizing hydrocarbons into high-octane gasoline components compared to supported catalyst made by existing methods. Additionally, BTEX compounds may be used as valuable intermediates in further chemical reaction processes to make polymers, fibers, and other materials.

Figure 3:
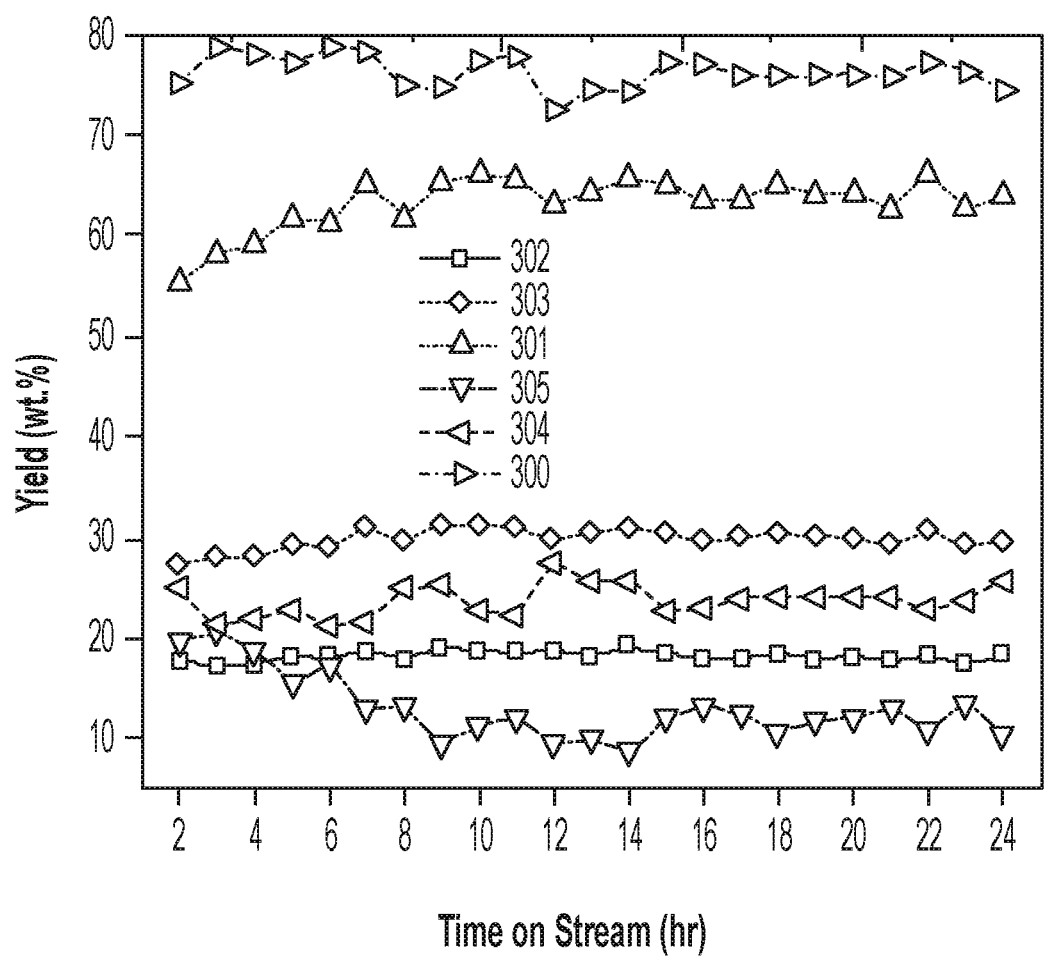
FIG. 3 graphically depicts the catalytic performance of each of the catalyst compositions represented in FIG. 2, according to one or more embodiments described in the present disclosure.

To confirm the suitability of Example 1 for long-term aromatization, Example 1 was further tested according to the above conversion condition for 24 hours. As seen in FIG. 3, the total aromatic conversion, which is denoted as reference number 300, remains consistent above 70% over the testing period. Specifically, BTEX conversion, which is denoted as reference number 301, improves until the 8$^{th}$ hour of testing and levels off well above 60% during the testing period. Likewise, the conversion rates of benzene 302 and toluene 303 remain relatively consistent over the testing period. While the amount of total paraffins and olefins 304 remains consistent over the testing period, the conversion rate of C9+ compounds 305 in fact decreases. Therefore, Example 1 is a suitable catalyst for aromatizing hydrocarbons, especially for aromatizing hydrocarbons into valuable BTEX components.

In a first aspect of the present disclosure, a process for aromatizing hydrocarbons includes contacting the hydrocarbons with a catalyst composition comprising a metal oxide dispersed on surfaces of a zeolite support, where contacting the hydrocarbons with the catalyst composition may cause at least a portion of the hydrocarbons to undergo a chemical reaction to form aromatic hydrocarbons. The catalyst composition is prepared by a synthesis process that includes combining the zeolite support with a hydrocarbon solvent to form a zeolite mixture, where the hydrocarbon solvent pre-wets the pores of the zeolite support and combining a polar solvent comprising a metal salt with the zeolite mixture to form an impregnated zeolite support. The synthesis may further include drying the impregnated zeolite support and calcining the impregnated zeolite support to convert the metal salt to the metal oxide, thereby forming the catalyst composition.

A second aspect of the present disclosure may include the first aspect, where the hydrocarbons may comprise linear or cyclic alkanes, alkenes, alkynes, or combinations of these hydrocarbons having from 1 carbon atom to 9 carbon atoms.

A third aspect of the present disclosure may include either of the first or second aspects, where the hydrocarbons may comprise light naphtha comprising at least 50 weight percent alkanes and having a boiling point from 30° C. to 90° C., based on the total weight of the light naphtha.

A fourth aspect of the present disclosure may include any of the first through third aspects, where the aromatic hydrocarbons may comprise benzene, toluene, ethylbenzene, xylene, or combinations of these aromatic hydrocarbons.

A fifth aspect of the present disclosure may include any of the first through fourth aspects, where the zeolite support may comprise a mordenite framework inverted (MFI) structured silica zeolite.

A sixth aspect of the present disclosure may include the fifth aspect, where the MFI structured silica zeolite may comprise a silica to alumina molar ratio from 5:1 to 50:1.

A seventh aspect of the present disclosure may include the fifth aspect, where the zeolite support may be a ZSM-5 zeolite.

An eighth aspect of the present disclosure may include any of the first through seventh aspects, where the metal oxide of the catalyst composition may comprise one or more oxides of a metal selected from groups 4-13 of the IUPAC periodic table.

A ninth aspect of the present disclosure may include the eighth aspect, where the metal oxide of the catalyst composition may comprise one or more oxides of a metal selected from periods 4-6 of the IUPAC periodic table.

A tenth aspect of the present disclosure may include any of the first through ninth aspects, where the metal oxide of the impregnated zeolite support may comprise one or more oxides of gallium, zinc, iron, hafnium, or combinations of these metals.

An eleventh aspect of the present disclosure may include any of the first through tenth aspects, where the catalyst composition may comprise from 1 weight percent to 50 weight percent metal oxide, based on the total weight of the catalyst composition.

A twelfth aspect of the present disclosure may include any of the first through eleventh aspects, where the metal salt may comprise a metal nitrate salt, a metal chloride salt, a metal sulfate salt, or combinations of these metal salts.

A thirteenth aspect of the present disclosure may include any of the first through twelfth aspects, where the hydrocarbon solvent may have a Hildebrand solubility parameter from 14.0 MPa$^{1/2}$ to 19.0 MPa$^{1/2}$.

A fourteenth aspect of the present disclosure may include any of the first through thirteenth aspects, where the hydrocarbon solvent may comprise an alkane having the chemical formula $C_nH_{2n+2}$, where n is from 3 to 12.

A fifteenth aspect of the present disclosure may include any of the first through fourteenth aspects, where the hydrocarbon solvent may comprise n-hexane, n-pentane, n-heptane, cyclohexane, n-octane, iso-octane, benzene, toluene, xylene, or combinations of these hydrocarbon solvents.

A sixteenth aspect of the present disclosure may include any of the first through fifteenth aspects, where the polar solvent may have a Hildebrand solubility parameter from 15.0 MPa$^{1/2}$ to 50.0 MPa$^{1/2}$.

A seventeenth aspect of the present disclosure may include any of the first through sixteenth aspects, where the polar solvent may have a dielectric constant of greater than 10.

An eighteenth aspect of the present disclosure may include any of the first through seventeenth aspects, where the polar solvent may comprise a halogenated hydrocarbon, water, or combinations of the polar solvents.

A nineteenth aspect of the present disclosure may include any of the first through eighteenth aspects, where combining the polar solvent comprising the metal salt with the mixture to form the impregnated zeolite support may comprise combining the polar solvent with the metal salt to form a metal salt mixture and combining the metal salt mixture with the zeolite mixture to produce an impregnated zeolite support mixture comprising the impregnated zeolite support.

A twentieth aspect of the present disclosure may include any of the first through nineteenth aspects, which may further comprise pretreating the catalyst composition under nitrogen or hydrogen flow at a temperature from 400° C. to 700° C. for a duration from 1 hour to 5 hours.

A twenty-first aspect of the present disclosure may include any of the first through nineteenth aspects, which may further comprise forming the catalyst composition into a catalyst.

A twenty-second aspect of the present disclosure may include any of the first through twenty-first aspects, where the contacting step may be conducted at a weight hourly space velocity from 0.1 per hour to 20.0 per hour.

A twenty-third aspect of the present disclosure may include any of the first through twenty-second aspects, where the contacting step may be conducted at a temperature from 200° C. to 900° C.

A twenty-fourth aspect of the present disclosure may include any of the first through twenty-third aspects, where the contacting step may be conducted at a pressure from 1 bar to 30 bars.

In a twenty-fifth aspect of the present disclosure, a method of preparing a catalyst composition may include preparing a mixture of a zeolite support with a hydrocarbon solvent to form a suspension, where the hydrocarbon solvent pre-wets the pores of the zeolite support; combining a polar solvent comprising a metal salt with the suspension to form an impregnated zeolite support; drying the impregnated zeolite support; and calcining the impregnated zeolite support to convert the metal salt to a metal oxide, thereby forming the catalyst composition.

A twenty-sixth aspect of the present disclosure may include the twenty-fifth aspect, where the zeolite support may comprise a mordenite framework inverted (MFI) structured silica zeolite.

A twenty-seventh aspect of the present disclosure may include the twenty-sixth aspect, where the MFI structured silica zeolite may comprise a silica to alumina molar ratio from 5:1 to 50:1.

A twenty-eighth aspect of the present disclosure may include the twenty-fifth or twenty-sixth aspects, where the zeolite support may be a ZSM-5 zeolite.

A twenty-ninth aspect of the present disclosure may include any of the twenty-fifth through twenty-eighth aspects, where the metal oxide of the catalyst composition may comprise one or more oxides of a metal selected from groups 4-13 of the IUPAC periodic table.

A thirtieth aspect of the present disclosure may include any of the twenty-fifth through twenty-ninth aspects, where the metal oxide of the catalyst composition may comprise one or more oxides of a metal selected from periods 4-6 of the IUPAC periodic table.

A thirty-first aspect of the present disclosure may include any of the twenty-fifth through thirtieth aspects, where the metal oxide of the impregnated zeolite support may comprise one or more oxides of gallium, zinc, iron, hafnium, or combinations of these metals.

A thirty-second aspect of the present disclosure may include any of the twenty-fifth through thirty-first aspects, where the catalyst composition may comprise from 1 weight percent to 50 weight percent metal oxide, based on the total weight of the catalyst composition.

A thirty-third aspect of the present disclosure may include any of the twenty-fifth through thirty-second aspects, where the metal salt may comprise a metal nitrate salt, a metal chloride salt, a metal sulfate salt, or combinations of these materials.

A thirty-fourth aspect of the present disclosure may include any of the twenty-fifth through thirty-third aspects, where the hydrocarbon solvent may have a Hildebrand solubility parameter from 14.0 MPa$^{1/2}$ to 19.0 MPa$^{1/2}$.

A thirty-fifth aspect of the present disclosure may include any of the twenty-fifth through thirty-fourth aspects, where the hydrocarbon solvent may comprise an alkane having the chemical formula $C_nH_{2n+2}$, where n is from 3 to 12.

A thirty-sixth aspect of the present disclosure may include any of the twenty-fifth through thirty-fifth aspects, where the hydrocarbon solvent may comprise n-hexane, n-pentane, n-heptane, cyclohexane, n-octane, iso-octane, benzene, toluene, xylene, or combinations of these hydrocarbon solvents.

A thirty-seventh aspect of the present disclosure may include any of the twenty-fifth through thirty-sixth aspects, where the polar solvent may have a Hildebrand solubility parameter from 15.0 MPa$^{1/2}$ to 50.0 MPa$^{1/2}$.

A thirty-eighth aspect of the present disclosure may include any of the twenty-fifth through thirty-seventh aspects, where the polar solvent may have a dielectric constant of greater than 10.

A thirty-ninth aspect of the present disclosure may include any of the twenty-fifth through thirty-eighth aspects, where the polar solvent may comprise a halogenated hydrocarbon, water, or combinations of the polar solvents.

A fortieth aspect of the present disclosure may include any of the twenty-fifth through thirty-ninth aspects, where combining the polar solvent comprising the metal salt with the mixture to form the impregnated zeolite support may comprise combining the polar solvent with the metal salt to form a metal salt mixture and combining the metal salt mixture with the zeolite mixture to produce an impregnated zeolite support mixture comprising the impregnated zeolite support.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter.

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for aromatizing hydrocarbons, the process comprising:
   contacting the hydrocarbons with a catalyst composition comprising gallium oxide dispersed on surfaces of a zeolite support, where the catalyst composition is prepared by a synthesis process comprising:
   combining the zeolite support with a hydrocarbon solvent to form a zeolite mixture, where the hydrocarbon solvent pre-wets the pores of the zeolite support,
   combining a polar solvent comprising a gallium salt with the zeolite mixture to form an impregnated zeolite support mixture, where the volume of the impregnated zeolite support mixture increases throughout the combining of the polar solvent,
   drying the impregnated zeolite support mixture to form an impregnated zeolite support, and
   calcining the impregnated zeolite support to convert the gallium salt to the gallium oxide, thereby forming the catalyst composition; and
   where contacting the hydrocarbons with the catalyst composition causes at least a portion of the hydrocarbons to undergo a chemical reaction to form aromatic hydrocarbons.

2. The process of claim 1, where the hydrocarbons comprise linear or cyclic alkanes, alkenes, alkynes, or combinations of these hydrocarbons having from 1 carbon atom to 9 carbon atoms.

3. The process of claim 1, where the hydrocarbons comprise light naphtha comprising at least 50 weight percent alkanes and having a boiling point from 30° C. to 90° C., based on the total weight of the light naphtha.

4. The process of claim 1, where the aromatic hydrocarbons comprise benzene, toluene, ethylbenzene, xylene, or combinations of these aromatic hydrocarbons.

5. The process of claim 1, where the zeolite support comprises a mordenite framework inverted (MFI) structured silica zeolite comprising a silica to alumina molar ratio from 5:1 to 50:1.

6. The process of claim 1, where the catalyst composition comprises from 1 weight percent to 50 weight percent gallium oxide, based on the total weight of the catalyst composition.

7. The process of claim 1, where the gallium salt comprises a gallium nitrate salt, a gallium chloride salt, a gallium sulfate salt, or combinations of these gallium salts.

8. The process of claim 1, where the hydrocarbon solvent comprises n-hexane, n-pentane, n-heptane, cyclohexane, n-octane, iso-octane, benzene, toluene, xylene, or combinations of these hydrocarbon solvents.

9. The process of claim 1, where the polar solvent comprises a halogenated hydrocarbon, water, or combinations of the polar solvents.

10. The process of claim 1, where combining the polar solvent comprising the gallium salt with the zeolite mixture to form the impregnated zeolite support comprises:
   combining the polar solvent with the gallium salt to form a gallium salt mixture; and
   combining the gallium salt mixture with the zeolite mixture to produce an impregnated zeolite support mixture comprising the impregnated zeolite support.

11. The process of claim 1, further comprising, before the contacting, pretreating the catalyst composition under nitrogen or hydrogen flow at a temperature from 400° C. to 700° C. for a duration from 1 hour to 5 hours.

12. The process of claim 1, where the contacting step is conducted at a weight hourly space velocity from 0.1 per hour to 20.0 per hour, a temperature from 200° C. to 900° C., and a pressure from 1 bar to 30 bars.

13. The process of claim 1, where the catalyst composition comprises 5 wt. % to 50 wt. % gallium oxide based on the total weight of the catalyst composition.

14. The process of claim 13, where the zeolite support comprises a ZSM-5 zeolite.

15. The process of claim 14, where the ZSM-5 zeolite has a silica to alumina molar ratio of 30:1.

\* \* \* \* \*